(12) United States Patent
Bogue et al.

(10) Patent No.: US 10,213,344 B2
(45) Date of Patent: Feb. 26, 2019

(54) DRESSING WITH MOISTURE INDICATOR

(71) Applicant: Availtek LLC, Carmel, IN (US)

(72) Inventors: Terri L. Bogue, Carmel, IN (US); Robert L. Bogue, Carmel, IN (US)

(73) Assignee: Availtek LLC, Carmel, IN (US)

( * ) Notice: Subject to any disclaimer, the term of this patent is extended or adjusted under 35 U.S.C. 154(b) by 378 days.

(21) Appl. No.: 14/951,342

(22) Filed: Nov. 24, 2015

(65) Prior Publication Data
US 2017/0143553 A1    May 25, 2017

(51) Int. Cl.
*A61F 13/00*    (2006.01)
*A61F 13/02*    (2006.01)
*A61M 25/02*    (2006.01)

(52) U.S. Cl.
CPC .. *A61F 13/00055* (2013.01); *A61F 13/00059* (2013.01); *A61F 13/0243* (2013.01); *A61M 25/02* (2013.01); *A61F 2013/00153* (2013.01); *A61F 2013/00182* (2013.01); *A61M 2025/0246* (2013.01)

(58) Field of Classification Search
CPC .......... A61F 13/00055; A61F 13/00059; A61F 13/0243; A61F 2013/00153; A61F 2013/00182; A61M 25/02; A61M 2025/0253
See application file for complete search history.

(56) References Cited

U.S. PATENT DOCUMENTS

| | | | | |
|---|---|---|---|---|
| 4,813,942 A * | 3/1989 | Alvarez | ................. | A61L 15/42 424/445 |
| 6,559,351 B1 * | 5/2003 | Eakin | ...................... | A61L 15/56 602/41 |
| 7,137,968 B1 * | 11/2006 | Burrell | ................. | A61M 25/02 604/180 |
| 2007/0060892 A1 * | 3/2007 | Propp | ................... | A61M 25/02 604/180 |

* cited by examiner

*Primary Examiner* — Ophelia A Hawthorne
(74) *Attorney, Agent, or Firm* — Maginot, Moore & Beck LLP

(57) ABSTRACT

A medical dressing includes an adhesive, permeable layer, a fabric support, and a hydrochromatic layer. The adhesive, permeable layer is configured to adhere to skin near a wound, for example, an intravenous catheter or other percutaneous device insertion site. The fabric support is disposed on the adhesive, permeable layer. The hydrochromatic layer is disposed on the fabric support, and is configured to change a color appearance responsive to contact with moisture.

19 Claims, 6 Drawing Sheets

DRESSING WITH MOISTURE INDICATOR

FIELD OF THE INVENTION

The present invention relates generally to medical dressings, and more particular, medical wound dressings.

BACKGROUND

Wound dressings are used for many purposes, including for wounds accidentally incurred, and those incurred to facilitate placement and protection of percutaneous medical devices. In an example of the latter, patients are in some cases provided with an intravenous catheter to infuse medication and/or nutrition necessary for treating or improving the patient's health condition. However, due to the invasive nature of the intravenous catheter, it is also a pathway for the introduction of bacteria and virus. Bacteria and/or viruses that enter the bloodstream via the intravenous catheter can cause infections that result in serious complications to the patient.

At present, there are many protocols, procedures, and products designed to prevent or inhibit this type of infection. For example, one of the primary products used to protect the insertion site and the intravenous catheter is a dressing. The dressing is typically a transparent, semi-permeable membrane attached to the body via an adhesive. In use, the dressing is placed over the insertion site and surrounding area to prevent the entry of bacteria and viruses that can travel into the bloodstream via the catheter insertion site. The semi-permeable nature of the dressing is required to allow moisture to evaporate through the dressing in order to keep the insertion site dry. However, a drawback is that the semi-permeable nature also creates the opportunity for environmental contaminants including bacteria to reach the insertion site when contaminated by moisture. This moisture also provides a breeding ground for bacteria around the insertion site.

Health care providers therefore monitor dressings to determine if they require changing based on a number of factors, including the presence of moisture. For example, health care providers monitor dressings to assess whether the dressing has become contaminated by body fluids or other materials. Some contaminants, such as blood, are highly visible and thus their presence is readily detected. However, many contaminants are clear or semi-clear fluids that are not as easily detected by visual inspection.

Accordingly, there exists a need for methods and apparatus that can improve the detectability of contaminants in dressings associated with intravenous catheter insertion sites, as well as other dressings.

SUMMARY OF THE INVENTION

At least some embodiments of the present invention address the above-stated needs, as well as others, by providing a dressing having a hydrochromatic substance affixed to the fabric portion of the dressing. The hydrochromatic substance changes color responsive to contact with moisture. The change in color can be more readily detected, thereby easing the detection of fluid contamination of the dressing.

A first embodiment is a medical dressing that includes an adhesive, permeable layer, a fabric support, and a hydrochromatic layer. The adhesive, permeable layer is configured to adhere to skin near a wound, which may include by way of non-limiting example, an intravenous catheter insertion site. The fabric support is disposed on the adhesive, permeable layer. The hydrochromatic layer is disposed on the fabric support, and is configured to change a color appearance responsive to contact with moisture found beneath or above the dressing.

A second embodiment is a method that includes applying a dressing to a percutaneous device insertion site, such as an intravenous catheter insertion site. The dressing includes an adhesive, permeable layer configured to adhere to skin near the insertion site a fabric support disposed on the adhesive, permeable layer, and a hydrochromatic layer disposed on the fabric support. The hydrochromatic layer is configured to change a color appearance responsive to contact with moisture. The method includes removing the dressing based on identification of a changed color appearance of the dressing indicating the presence of moisture. The method also includes applying a subsequent dressing to the intravenous catheter insertion site.

The above-described features and advantages, as well as others, will become more readily apparent to those of ordinary skill in the art by reference to the following detailed description and accompanying drawings.

DETAILED DESCRIPTION

Figure 1:
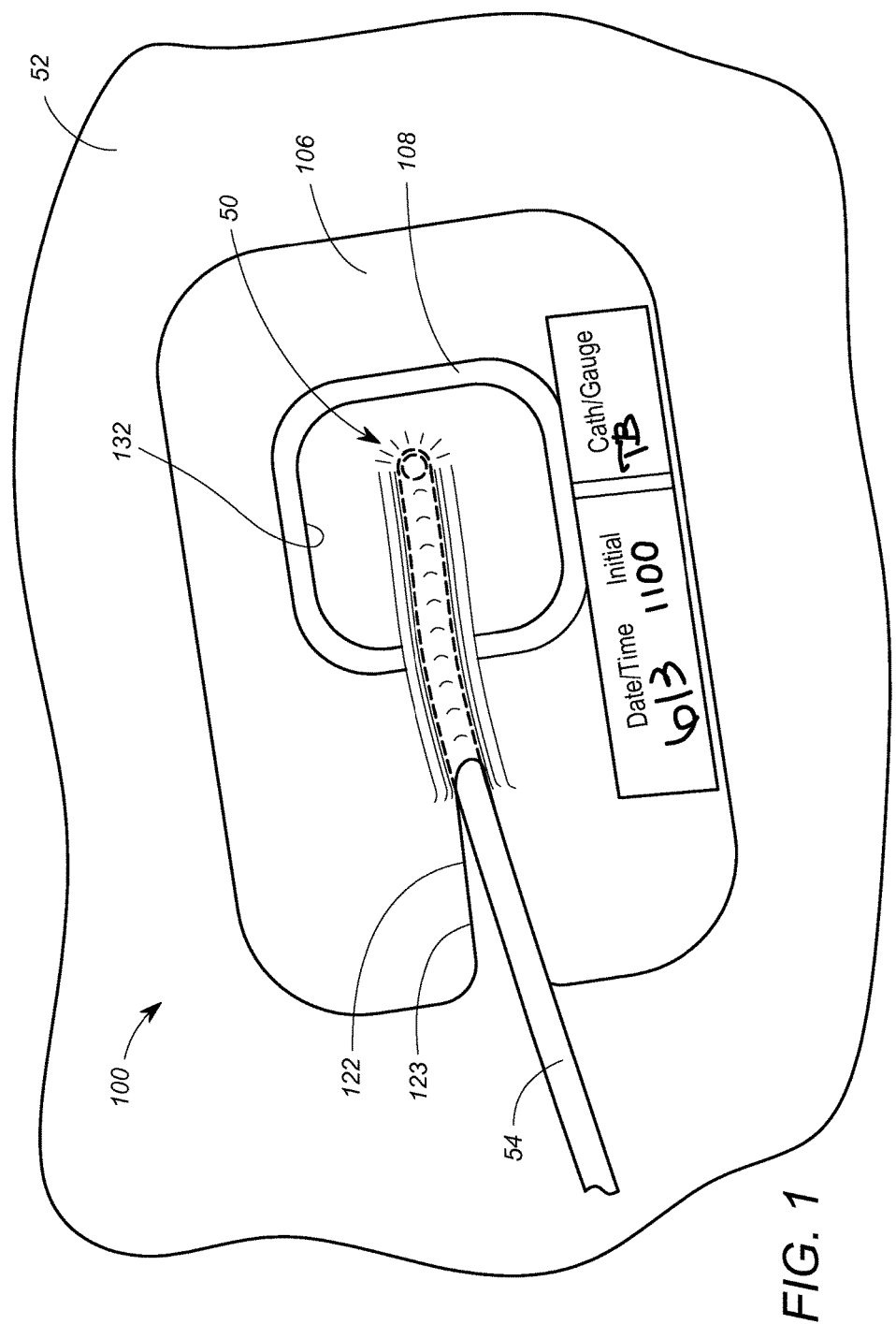
FIG. 1 shows a perspective view a wound dressing according to a first embodiment of the invention in use at an insertion site of an intravenous catheter of a patient.
Figure 2:
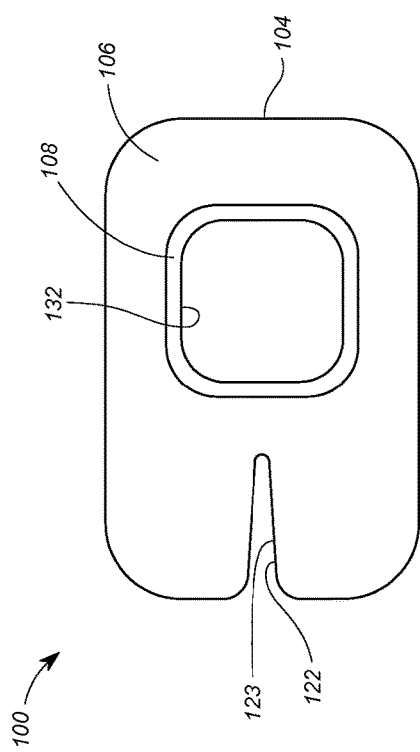
FIG. 2 shows a top plan view of the wound dressing of FIG. 1 apart from the patient.

FIG. 1 shows a perspective view a wound dressing 100 according to a first embodiment of the invention in use at an insertion site 50 of an intravenous catheter or central line 54 of a patient 52. Only a portion of the patient 52 immediately surrounding the insertion site 50 is shown in FIG. 1. Those of ordinary skill in the art would understand the appropriate insertion sites for each patient based on medical needs and physiological characteristics. In other embodiments, the insertion site 50 may be an insertion site of another type of percutaneous device, or even another type of wound. FIG. 2 shows a top plan view of the wound dressing 100, and FIG. 3 shows an exploded perspective view of the wound dressing 100.

Figure 3:
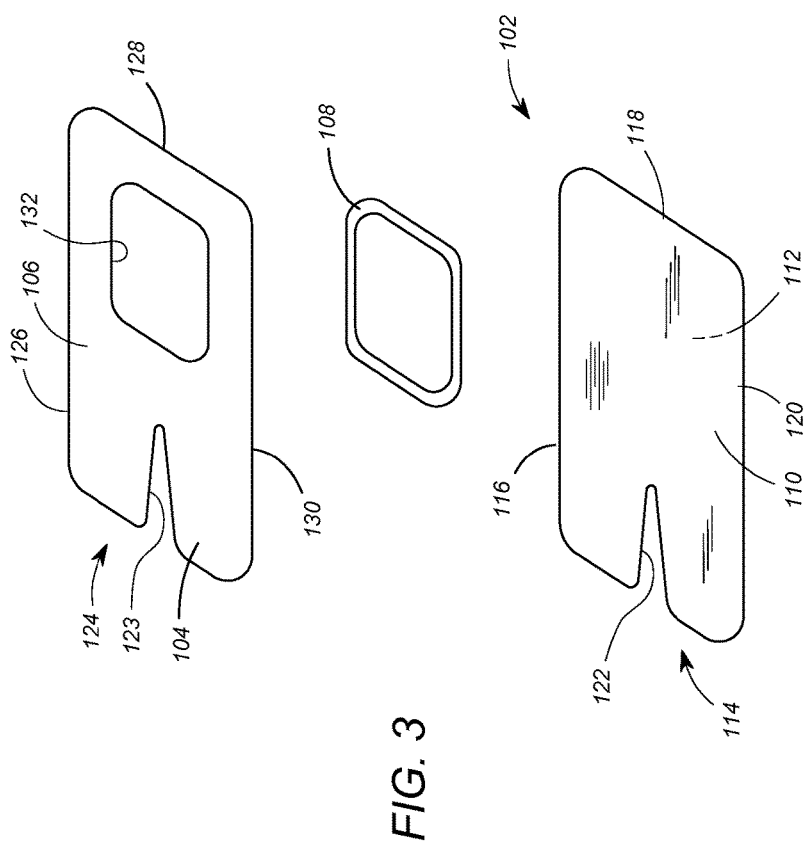
FIG. 3 shows an exploded perspective view of the wound dressing of FIG. 2.

With reference to FIGS. 1, 2 and 3, the wound dressing 100 is particularly configured as an intravenous catheter dressing that includes an adhesive layer or substrate 102, a fabric mesh support 104, and a hydrochromatic layer 106. In this embodiment, the wound dressing 100 also includes an optional fabric window ridge 108. However, it will be appreciated that other embodiments need not include such a fabric window ridge.

In this embodiment, the adhesive substrate 102 is a clear polymer sheet having a top surface 110 and bottom surface 112. The bottom surface 112 is coated with an adhesive that is configured to adhere to flesh in the vicinity of a wound, such as the area surrounding an intravenous catheter insertion site (e.g. site 50 of FIG. 1). Such adhesive materials are known. The adhesive substrate 102 has a generally rectangular shape having four sides 114, 116, 118 and 120 with rounded corners therebetween. The first side 114 of the adhesive layer 102 in this exemplary embodiment includes an optional V-shaped notch 122 generally defined in the center of the first side 114. The V-shaped notch 122 this allows for easier positioning and securing of dressing around the intravenous catheter 54. However, it will be appreciated that other embodiments need not include such a notch. The adhesive substrate 102 is permeable to allow gas and liquid to pass therethrough. As is known in the art the adhesive substrate 102 is permeable to allow perspiration to evaporate away from the wound. However, it is this permeability that can undesirably allow external liquids (including body fluids, vomitus, and food or drink) that contact the dressing 100 to pass to the wound.

The fabric mesh support 104 is a sheet of fabric mesh material that is affixed to and provides mechanical strengthening and support to the adhesive substrate 102. Preferably, the fabric mesh support 104 has a similar shape as the adhesive substrate 102 to provide support throughout. Accordingly, in this embodiment, the fabric mesh support 104 has four sides 124, 126, 128 and 130 that have a length and shape substantially equivalent to the respective four sides 114, 116, 118 and 120. The first side 124 has a V-shaped notch 123 that aligns with the V-shaped notch 122, if present.

The mesh support 104 is generally opaque. However, to allow visual inspection of the insertion site 50, the fabric mesh support 104 includes an interior void 132. Thus, a patient or medical professional may view the intravenous site through the portion of the transparent adhesive substrate 102 that is co-located with the interior void 132.

The fabric window ridge 108 is a thicker piece of mesh or fabric that is configured in the shape of the interior void 132, and disposed about the interior void 132 between the fabric mesh support 104 and the adhesive substrate 104. The fabric window ridge 108 is optional, but is included in this embodiment to absorb small amounts of fluid or blood leaking from insertion site 50. The fabric window ridge 108 and the fabric mesh support 104 are affixed to the adhesive substrate 102 using conventional means, such as an adhesive.

The hydrochromatic layer 106 is disposed on the fabric mesh support 104. The hydrochromatic layer 106 is applied to the fabric mesh support 104 as a liquid (e.g. ink) that cures as a coating on the fabric mesh support 104. Thus, the hydrochromatic 106 and fabric mesh support 104 are shown as the same structure in FIGS. 1, 2 and 3. The hydrochromatic layer 106 is a material configured to change a color appearance responsive to contact with moisture. In this embodiment, the hydrochromatic layer 106 is configured to appear white or near white until it comes in to contact with moisture, at which point it becomes "clear" or at least partly transparent. In such embodiment, the fabric mesh support 104 has a non-white color or color coating, or includes a non-white colored pattern. Thus, when the hydrochromatic layer 106 comes into contact with moisture, the non-white color or non-white colored pattern on the fabric mesh support 104 is revealed. Preferably, the non-white color is a different hue than white, and may be red, yellow, orange, red, blue, violet or other common hues or mixtures thereof. Even a sharply contrast black or grey may be employed.

Figure 4:
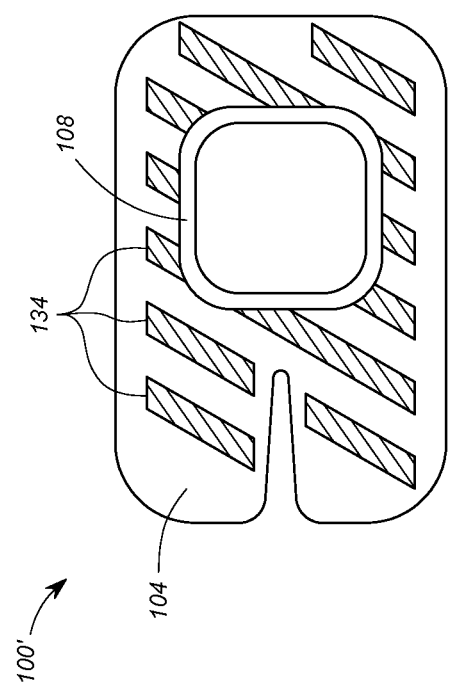
FIG. 4 shows a top plan view of a portion of the wound dressing of FIG. 2 apart from the hydrochromatic layer.

To this end, FIG. 4 shows a top play view of the fabric mesh support 104 applied without the hydrochromatic layer 106. The fabric mesh support 104 includes a highly visible, non-white pattern 134 applied thereon. The non-white pattern 134 constitutes a colored ink pattern printed on the fabric mesh support 104 in a pattern using any suitable method. In the embodiment of FIG. 4, the non-white pigment is applied in a pattern of diagonal stripes. FIG. 2 shows the wound dressing 100 after the hydrochromatic layer 106 has been applied to the wound dressing. The hydrochromatic layer 106 may also be printed on the fabric mesh support over the non-white pattern 134.

Figure 5:
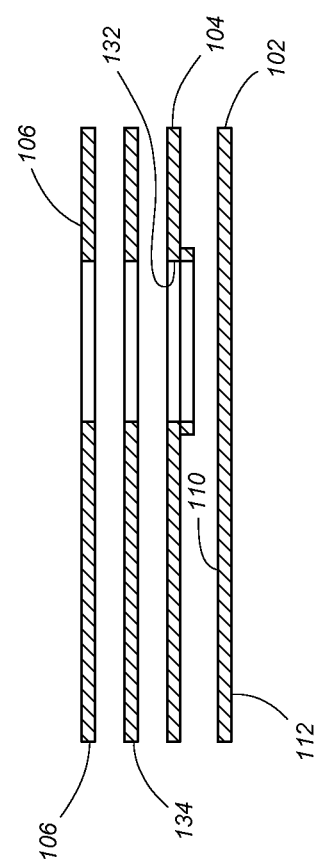
FIG. 5 shows a schematic depiction of the layers of the wound dressing of FIG. 2.

FIG. 5 shows an exploded schematic cutaway side view of the dressing 100. FIG. 5 is not to scale, and represents printed ink layer (e.g. 106, 134) as separate layers even though they can penetrate spaces between fibers of the mesh support 104. As shown in FIG. 5, the non-white pattern 134 (which may also be a solid pattern) is applied to the entire fabric mesh support 104 except within the void 132. Similarly, the hydrochromatic layer 106 is applied to the entire mesh support 104 (over the pattern 134) except within the void 132.

In this embodiment, the hydrochromatic layer 106 may suitably be the number 1901 hydrochromatic white ink available from Matsui International Company, Inc. of Gardena, Calif. As discussed above, the hydrochromatic layer 106 in this embodiment is white or near white, and becomes substantially transparent when it is damp or exposed to liquid, thus revealing the non-white pattern 134 or layer underneath. It will be appreciated that although the non-white pattern 134 is shown as thick diagonal stripes in FIG. 4, the non-white pattern 134 may take other shapes, and can even include a solid color "pattern", where the layer 134 is simply a solid color.

It will be appreciated that any conventional dressing for an intravenous catheter, wherein the dressing has an adhesive substrate and mesh support, may be converted to a liquid-signaling dressing according to embodiments of the present invention. In one exemplary manufacturing method, the adhesive substrate 102 and the mesh support 104 are assembled in a conventional manner. A highly-visible pattern such as the non-white pattern 134 is printed or otherwise applied to the top of the mesh support 104. After these steps, the partially constructed wound dressing 100' may suitably have the appearance of that shown in FIG. 4.

Thereafter, the hydrochromatic layer 106 is printed or otherwise applied to cover the non-white pattern 134. After such application, the wound dressing 100 may suitably have the appearance as shown in FIG. 2. It will be appreciated that one or two peelable (e.g. wax paper) strips, not shown, but which are known in the art, are applied to the adhesive surface 112 of the adhesive substrate 102 to protect the adhesive surface 112 until it is ready for application to a patient. The wound dressing 100 is thus complete.

With reference to FIGS. 1 to 6, use of the dressing 100 involves insertion of an intravenous catheter 54 at the properly prepared insertion site 50 using conventional methods. The wound dressing 100 is then applied to the insertion site 50 in a conventional manner, as shown in FIG. 1. The dressing 100 has the general appearance as shown in FIG. 2. However, if a liquid is spilled on or otherwise comes into contact with the hydrochromatic layer 106, the portion of the hydrochromatic layer 106 that becomes wet changes to the transparent color, thereby revealing at least a portion of the underlying pattern 134. This visual change related to liquid coming into contact with the hydrochromatic layer 106 also occurs when moisture from the patient under the dressing comes into contact with the hydrochromatic layer.

Figure 6:
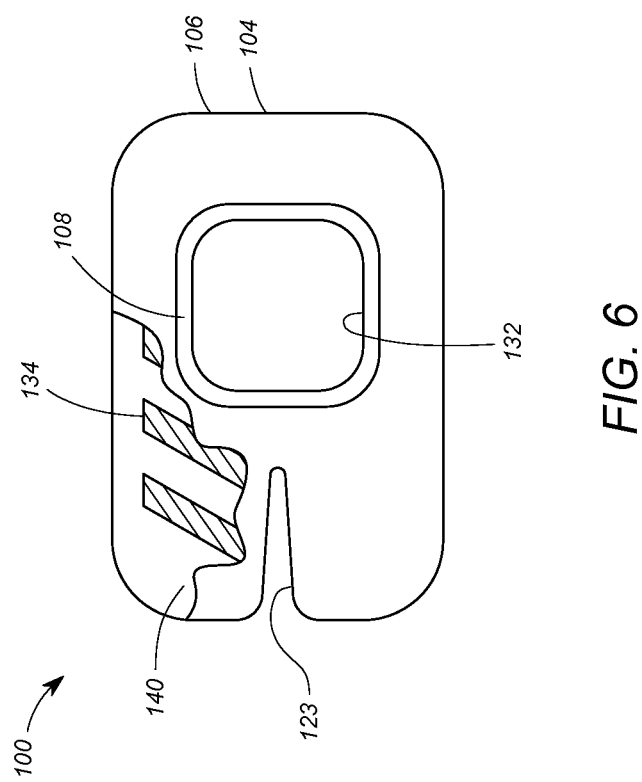
FIG. 6 shows a top plan view of the wound dressing of FIG. 2 wherein liquid has come into contact with a portion of the hydrochromatic layer.

FIG. 6 shows a top plan view of the dressing 100 where liquid has come into contact with a portion 140. The portion 140 consists of the area in which the hydrochromatic layer 106 has changed color to reveal the underlying pattern 134. The liquid, for example, may be drink that is spilled by the patient or various body or intravenous fluids or drainage leaking from the insertion site that may come in contact with the dressing. As discussed above, many liquids from beneath or external to the wound or intravenous dressing can be sources and causes of secondary infections. By revealing the underlying pattern 134, the patient and/or caregiver can detect that the dressing has become wet and potentially contaminated. The caregiver can then cause the dressing 100 to be changed to a new dressing, preferably of the same design as the dressing 100.

It will be appreciated that the dressing 100 may take other conventional shapes for intravenous line insertion dressings. The void 132 may take other shapes as well, without departing from the principles of the invention. It will further be appreciated that the hydrochromatic layer 106 may take other forms. For example, the hydrochromatic layer 106 may suitably be non-white color that changes to a clear color when exposed to liquid. In such a case, the pattern 134 may suitably be white (patterned or solid white), or a non-white pattern or solid color that is different from the non-white color of the dry hydrochromatic layer 106. Furthermore, the hydrochromatic layer 106 may suitably be a first solid color that changes into a second solid color when exposed to liquid. In such a case, the pattern 134 may be eliminated entirely.

Embodiments of the present invention thereby provide a method and apparatus that can be used to detect the presence of liquid from beneath or on the external side of an intravenous line dressing, or other percutaneous device dressing. By early detection of moisture or spillage, secondary infection of the wound site can be avoided, resulting in reduced negative health results. In addition, costs associated with treatment of secondary infections may be avoided.

In will be appreciated that the above-described embodiments are merely illustrative, and that those of ordinary skill in the art may readily devise their own implementations and modifications that incorporate the principles of the present invention and fall within the spirit and scope thereof.

What is claimed is:

1. A medical dressing comprising:
an adhesive, permeable layer configured to adhere to skin near a wound;
a fabric support disposed on the adhesive, permeable layer;
a hydrochromatic layer disposed on the fabric support configured to change a color appearance responsive to contact with moisture; and
wherein each of the permeable layer and the fabric support define an outer periphery, the outer periphery having a notch therein defining an entry point for a percutaneous device, and wherein the fabric support includes a void spaced apart from the notch, the void configured to align with a percutaneous device insertion site when said dressing is applied to the wound.

2. The medical dressing of claim 1, wherein the adhesive, permeable layer comprises a transparent material.

3. The medical dressing of claim 2, wherein the permeable layer includes four sides, a first side of the four sides having a notch defining an entry point for a percutaneous device.

4. The medical dressing of claim 3, wherein the fabric support includes a void that exposes at least an internal portion of the adhesive, permeable layer, the void configured to align with a percutaneous device insertion site.

5. The medical dressing of claim 4, wherein the percutaneous device is an intravenous catheter.

6. The medical dressing of claim 1, further comprising a patterned color layer disposed on the fabric support between the hydrochromatic layer and the fabric, and wherein the hydrochromatic layer is configured to change a visibility of the patterned color layer responsive to contact with moisture.

7. The medical dressing of claim 6, wherein the patterned color layer includes a solid color pattern.

8. The medical dressing of claim 6, wherein:
the hydrochromatic layer conceals the patterned color layer when the hydrochromatic layer is not exposed to moisture;
the hydrochromatic layer reveals the patterned color layer when the hydrochromatic layer is exposed to moisture.

9. The medical dressing of claim 1, wherein the adhesive, permeable layer is configured to adhere to skin near the percutaneous device.

10. The method dressing of claim 9, wherein the percutaneous device comprises an intravenous catheter.

11. A medical dressing comprising:
an adhesive, permeable layer configured to adhere to skin near a wound, the adhesive, the permeable layer comprising a transparent material;
a fabric support disposed on the adhesive, permeable layer;
a hydrochromatic layer disposed on the fabric support configured to change a color appearance responsive to contact with moisture; and
wherein each of the permeable layer and the fabric support define an outer periphery, wherein the fabric support includes an interior void spaced apart from the outer periphery, the interior void configured to allowing viewing of the percutaneous device insertion site through the adhesive, permeable layer when the dressing is applied to the wound.

12. The medical dressing of claim 11, further comprising a patterned color layer disposed on the fabric support between the hydrochromatic layer and the fabric, and wherein the hydrochromatic layer is configured to change a visibility of the patterned color layer responsive to contact with moisture.

13. The medical dressing of claim 12, wherein the patterned color layer includes a solid color pattern.

14. The medical dressing of claim 12, wherein:
the hydrochromatic layer conceals the patterned color layer when the hydrochromatic layer is not exposed to moisture;
the hydrochromatic layer reveals the patterned color layer when the hydrochromatic layer is exposed to moisture.

15. The medical dressing of claim 11, further comprising a fabric ridge extending around the void, the fabric ridge having a thickness greater than that of the fabric support.

16. A method, comprising:
applying a dressing to a percutaneous device insertion site, the dressing including an adhesive, permeable layer configured to adhere to skin near the percutaneous device insertion site, a fabric layer disposed on the adhesive, permeable layer, and a hydrochromatic layer disposed on the fabric layer configured to change a color appearance responsive to contact with moisture, wherein each of the permeable layer and the fabric layer define an outer periphery, the outer periphery having a notch therein defining an entry point for a percutaneous device, and wherein the fabric support includes a void spaced apart from the notch, the void aligning with the percutaneous device insertion site;

removing the dressing responsive to identification of a changed color appearance indicating the presence of moisture; and applying a subsequent dressing to the percutaneous device insertion site.

17. The method of claim 16, wherein the dressing further comprises a patterned color layer disposed on the fabric support between the hydrochromatic layer and the fabric, and wherein the hydrochromatic layer is configured to change a visibility of the patterned color layer responsive to contact with moisture.

18. The method of claim 17, wherein:
the hydrochromatic layer conceals the patterned color layer when the
hydrochromatic layer is not exposed to moisture.

19. The method of claim 16, wherein the percutaneous device insertion site comprises an intravenous catheter insertion site.

* * * * *